United States Patent [19]

Giles et al.

[11] Patent Number: 4,536,392

[45] Date of Patent: Aug. 20, 1985

[54] METHOD FOR CONTROLLING HEMOPHILIA IN MAMMALS

[75] Inventors: Alan R. Giles, Kingston, Canada; Kenneth G. Mann, Rochester, Minn.

[73] Assignee: Queen's University at Kingston, Kingston, Canada

[21] Appl. No.: 508,213

[22] Filed: Jun. 27, 1983

[51] Int. Cl.³ .............................................. A61K 35/16
[52] U.S. Cl. ................................... 424/101; 424/199; 514/786
[58] Field of Search ........................ 424/101, 199, 365

[56] References Cited

PUBLICATIONS

Nesheim et al.–J. of Biol. Chem., vol. 256, No. 13, Jul. 1981, pp. 6537–6540.

Giles et al.–Blood–vol. 59, No. 2, (Feb. 1982), pp. 401–407.

Nesheim et al.–Chem. Abst., vol. 95, (1981), p. 112612u.

Primary Examiner—Sam Rosen
Attorney, Agent, or Firm—Richard J. Hicks

[57] ABSTRACT

A method for controlling HemophiliaA (Antihemophilic Factor (F. VIII:C) deficiency) in mammals is described. Factor VIII:C deficiency in the mammal is bypassed by infusion of a synergistic mixture of a phospholipid and Factor Xa so that the cascade process of blood clotting may continue. The proportions of phospholipid and Factor Xa in the mixture are critical as too little Xa has no effect while too much is toxic (thrombogenic).

6 Claims, 1 Drawing Figure

METHOD FOR CONTROLLING HEMOPHILIA IN MAMMALS

FIELD OF INVENTION

This invention relates to the control of hemophilic bleeding in mammals. More particularly this invention relates to the therapeutic treatment of Factor VIII:C deficient patients by means of a Factor VIII:C bypass technique using a synergistic mixture of phospholipids with Factor Xa.

BACKGROUND OF INVENTION

Classic Hemophilia A is a sex-linked recessive inherited disorder of the blood where the activity of a specific coagulation factor (protein), required for the cascade or chain process for blood coagulation, is either reduced or absent. Hemophilia afflicts about 1 in 10,000 of the male population. This produces a severe bleeding disorder and constitutes the most frequently clinically encountered congential coagulation disorder. Since about 1965 the prognosis of affected individuals has considerably improved due to the availability of specific clotting factor replacement products derived from the blood of normal donors which can be transfused. These products contain the most usually absent factor, Factor VIII in a concentrated form. Unfortunately, however, approximately 10% of all treated hemophiliacs develop antibodies to the transfused Factor VIII:C and become untreatable by this means. It is an aim of the present invention to provide a method for the treatment and management of such antibody sensitized hemophiliacs.

DISCUSSION OF PRIOR ART

Heretofore hemophiliacs with antibodies to F. VIII:C have been managed by various therapies none of which are satisfactory. The use of immunosuppressive therapy is morbidity. The use of Factor VIII:C derived from other species, i.e. porcine or bovine, has been shown to be an effective replacement but may be associated with major side effects due to the development of heterologous antibodies. Recently considerable interest has been shown in using prothrombin complex concentrates (PCC). As explained in more detail hereinafter, blood coagulation proceeds by a series or cascade of activation steps where circulating inactive clotting factors (zymogens) are converted to proteolytic enzymes. The final product of the cascade is thrombin (IIa) which converts the sol protein, fibrinogen, to its gel form, fibrin. Recent work has demonstrated that Factor VIII:C is not a proteolytic enzyme but a potent co-factor of the activation step whereby Factor IXa activates Factor X to Xa. In classic Hemophilia A, this co-factor activity is reduced or missing so that insignificant activation of Factor X takes place despite all other clotting factors being present at normal levels. As noted above, transfusion of Factor VIII:C concentrates can correct this abnormality and similar concentrates have been developed for the congenital deficiency of Factor IX. These concentrates differ from those of Factor VIII:C in containing significant quantities of other clotting factors namely X, VII and II (prothrombin). Moreover, it is the rule that all concentrates contain trace contaminents of the activated products of these clotting factors, namely IXa, Xa, VIIa and IIa (thrombin). It will be noted that, with the exception of Factor IX, the remaining three clotting factors are placed in the cascade below the critically important Factor VIII:C-dependent step. It has been postulated, that these concentrates, by providing pre-formed activated products, may achieve Factor VIII:C bypassing activity (FEBA) in hemophiliacs where Factor VIII:C replacement is precluded by the development of antibodies to this clotting factor. Initial anecdotal clinical reports were promising but by no means unanimous. This lack of unanimity related to the uncertainty as to which, if any, of the component clotting factors were the most critical. The products used are of two types. The first are known as "unactivated" PCC and are products that have been developed specifically to replace deficiencies of the clotting factors that they contain. In such patients, it is considered undesirable to infuse preactivated clotting factors because of concern for thromboembolic side effects. Therefore, attempts are made, in the fractionation process, to minimize the activated clotting factor content although all products contain some. As it was the activated clotting factor content that was considered to be the putative agent(s) in the treatment of hemophiliacs with inhibitors, some manufacturers have deliberately activated the PCC preparations for this purpose. These are known as "activated" PCC. Recent clinical trials have confirmed the benefit of the use of non-activated PCC as compared with placebo but the response was less than optimal in comparison to that which would be expected from conventional Factor VIII:C replacement in hemophiliacs without inhibitors. A similar study compared treatment with an unactivated PCC with an activated PCC prepared by the same manufacturer. There appeared to be a marginal benefit in favour of the activated preparation. Despite this, the response remained suboptimal and the absence of any clear indication as to the specific constituent of the preparation responsible for the effect seen, it is impossible to ensure inter-batch reproducibility of individual production lots of apparently the same product. As a result, there is still not universal agreement as to the validity of this approach.

In "Blood", v. 59, p. 401–407, Feb. 1982, Giles et al demonstrated that the in vivo thrombogenicity of prothrombin complex concentrates was highly correlated with their individual content of coagulant active phospholipid. However, this component alone was non-thrombogenic but required the presence of Factor Xa. At high dose, the latter was thrombogenic alone but its potency was drastically increased in the presence of small amounts of coagulant-active phospholipid. It was suggested that the combination of these two components accounted for the thrombogenicity associated with the use of prothrombin complex concentrates and evidence was presented that this thrombogenic effect could be mimicked by a combination of highly purified Factor Xa and phosphatidylcholinephosphatidylserine (PCPS) lipid vesicles. This confirmed the findings of Barton et al in the Journal of Lipid Research v. 11, p. 87, 1970, who used less well-defined protein/lipid components.

SUMMARY OF INVENTION

As can be seen from FIG. 1, the presence of Factor Xa alone bypasses the requirement for Factor VIII:C. Although this is the case in vitro, in vivo the presence of a number of inhibitory processes complicate its use in achieving Factor VIII:C by passing activity. Combining this factor with coagulant-active phospholipid in the form of PCPS vesicles exerts an apparent synergistic activity in vivo presumably by mimicking the normal interactions between Factor Xa and platelet phospholipid. It has been demonstrated that the dose of each component administered is critical in that a minimum dose of Factor Xa/kg body weight is required and that the dose of phospholipid must be limited to avoid unacceptable toxicity (thrombogenicity).

Thus, by one aspect of this invention there is provided a method for controlling hemophilia in mammals comprising administering intravenously to said mammal a synergistic mixture of phospholipid vesicles and mammalian blood Factor Xa in relative proportions and in an amount just sufficient to arrest bleeding.

By another aspect of this invention there is provided a pharmaceutical composition for the treatment of hemophilia in mammals comprising a synergistic mixture of phospholipid vesicles and mammal blood Factor Xa in relative proportions just sufficient to arrest bleeding.

DETAILED DESCRIPTION OF THE INVENTION

Figure 1:
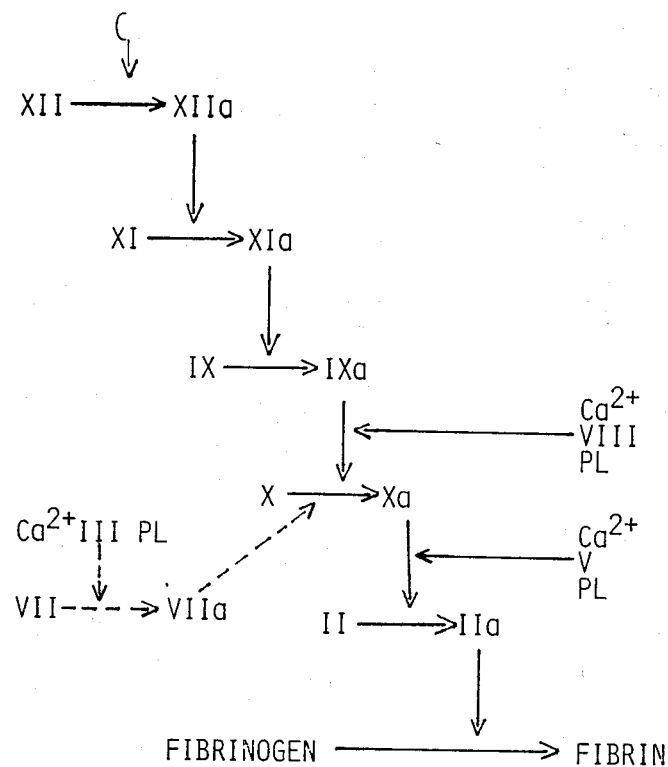
FIG. 1 is a schematic diagram illustrating the stages in the cascade process of blood clotting.

As shown in FIG. 1, blood coagulation proceeds by a series of activation steps where circulating inactive clotting factors are converted to proteolytic enzymes. The final product of this cascade is thrombin (IIa) which converts the sol protein, fibrinogen, to its gel form fibrin which is the basic constituent of a blood clot. Factor VIII:C is not a proteolytic enzyme but a potent co-factor of the activation step in which Factor IXa activates Factor X to Xa. Indeed Factor VIII:C is a rate limiting factor, in the absence or reduction of which activation of Factor X to Factor Xa is prevented or minimized even in the presence of normal levels of all other clotting factors. It is known that the complex of Factor Xa, Factor V and calcium responsible for the conversion of prothrombin (Factor II) to thrombin (Factor IIa) is assembled on a phospholipid surface provided by the platelet. It is proposed that the synergistic effect of highly-purified factor Xa in combination with PCPS vesicles provides a close approximation of the physiological event. The remaining components of the complex, i.e. Factor V and ionized calcium, being unaffected by the availability of Factor VIII:C, are available in the recipient's blood. Studies have demonstrated true synergism between the two components, i.e. Factor Xa and PCPS vesicles, in vivo. Decreasing the dose of Factor Xa can be accommodated by increasing the dose of PCPS and vice versa in achieving the same end-point, i.e. thrombin generation. It is now known, however, that thrombin has multiple roles in vivo and some of these are mutually antagonistic. As shown in FIG. 1, thrombin is the proteolytic enzyme required for the conversion of fibrinogen to fibrin. It is also known that thrombin is required to activate a Vitamin K-dependent protein, Protein C, which is a potent anticoagulant. This anticoagulant effect is achieved by the inactivation of the critically important cofactors, Factors VIII:C and V. It also appears to exert significant control over the fibrinolytic mechanism, i.e. the mechanism responsible for clearing fibrin formed by the conversion of fibrinogen by thrombin. It has been demonstrated that activated Protein C requires a phospholipid surface in order to exert its anticoagulant effect. Consequently, the Factor VIII:C bypassing effect, in achieving hemostasis, requires a critical dose ratio of Factor Xa to PCPS. This is calculated on a dose/kg body weight basis. The dose of Factor Xa is critical. Above a given level, unacceptable toxicity (thrombogenicity) occurs whereas below a certain level, a hemorrhagic tendency is produced in normal animals, i.e. VIII:C replete animals, presumably due to the relative excess of phospholipid favouring the anticogulant effect of activated Protein C.

Factor Xa may be obtained by fractionating plasma from normal donors to obtain the precursor zymogen Factor X which can then be activated by known procedures (Bajaj et al. J. Biol. Chem. 248:7729, 1973; Downing et al. J. Biol. Chem. 250:8897, 1975). Factor Xa may be stored indefinitely in 50% glycerol at $-20°$ C. The amount of Factor Xa in the dosage form is extremely small and sufficient quantities to treat large numbers of hemophiliacs can be derived from a small number of blood donors, in comparison to the many thousands required for the provision of more conventional therapy. This has distinct advantages, apart from the obvious one of economy. The accidental transmission of infection is a major hazard of multiple transfusion practice in patients such as hemophiliacs. Hepatitis and acquired immunodeficiency syndrome are major problems. By restricting the number of donors required, careful screening for these problems may be effected thus drastically reducing if not eliminating the risk. Furthermore, the purified Factor Xa, unlike many of the blood products presently used can be sterilized with relative ease, and in comparison to Factor VIII:C is relatively stable thus making it more suitable for use in areas where sophisticated hospital facilities are not available.

Phosphatidylcholine and phosphatidylserine are available commercially as semi-purified reagents. They are prepared from egg yolks and bovine brain respectively. The PCPS lipid vesicles may be prepared by a conventional and standardized protocol (Nesheim et al, J. Biol. Chem. 254: 10952, 1979 and Barenholz et al Biochem. J. 16:2806, 1976) which produces single compartment vesicles of uniform dimension (325–350 Å) which may be stored at 4° C. for 2 to 3 weeks. The molar ratio of phosphatidylserine to phosphatidylcholine is about 1:3, based on the relative amounts of these lipids used in the preparation of the vesicles.

The Factor Xa-PCPS mixture is freshly prepared by mixing Factor Xa and PCPS in the desired ratio immediately prior to use.

In order to demonstrate the efficacy of the treatment tests were carried out on both normal and specially bred hemophilic dogs, maintained on water ad libitum and regular dry dog Chow (Ralston-Purina, St. Louis, Mo.), as described in detail in Examples 1–7 hereinafter. The animals were anesthetized with a rapid acting intravenous barbiturate 5%–18 mg/kg body weight. A continuous infusion was established via a 21 gauge butterfly needle in the cephalic vein using isotonic saline for injection to keep the vein open. All medications were administered via this route. All hair was clipped from around the animal's claws and silicone grease was applied to prevent blood from tracking back beneath the claw. A spring loaded sliding blade guillotine was used to sever the apex of the nail cuticle which was visualized or located in relation to the dorsal nail groove. Blood was allowed to fall freely by positioning the paw over the edge of the operating table. In normal dogs bleeding stops abruptly (mean 6.0±3.7 (S.D.) mins)

whereas in hemophilic animals bleeding may stop transiently but always restarts and continues until arrested by the application of silver nitrate (Blood, Vol. 60, No. 3, P727-730 Sept. 1982). In all cases the dosage of Factor Xa/PCPS was administered on a dose/kg body weight basis. The dose of PCPS is unitized in arbitrary units. 1 Arbitrary unit PCPS equals $1 \times 10^{-8}$ moles of phospholipid as assayed by an inorganic phosphorus assay. Factor Xa is unitized according to an internationally accepted classification in which 1 unit of Factor X is the amount present in 1 ml of normal plasma and 1 unit of Factor Xa is the amount of activity present when 1 unit of Factor X is fully activated. The assay is standardized by measuring activity in the test preparation against the activity in a normal pool plasma standard as described by Suomela H et al (Thrombosis Research 10:267, 1977) as modified by Giles A. R. et al (Thrombosis Research 17; 353, 1980).

EXAMPLE 1

A normal dog was tested as described above, by cutting the cuticle of the right hind nail 4. Bleeding stopped spontaneously at 5 minutes but rebleeding occurred at 9 minutes for a further 3 minutes. 15 Minutes after the start of the first cuticle bleeding time, the animal was infused with PCPS/Xa at a dose of 40 units and 0.05 units/kg body weight respectively. 2 Minutes after this infusion, the right hind nail 3 was severed. Bleeding continued for 12 minutes and the cuticle required cautery with silver nitrate application. 60 Minutes after the infusion of PCPS/Xa, the right hind nail 2 was severed but bleeding ceased spontaneously after 7 minutes. It will be noted that the cuticle bleeding time was initially normal but became abnormal immediately after the infusion of PCPS/Xa at this dosage suggesting that the relative excess of PCPS had favoured the anticoagulant effect of activated Protein C, thus compromising the generation of fibrin normally required to cause bleeding to stop. This effect had dissipated 60 minutes after the infusion of PCPS/Xa.

EXAMPLE 2

This procedure of Example 1, showing the effect of PCPS/Xa at a dosage of 40 units and 0.05 units/kg body weight respectively on the cuticle bleeding time of a normal dog was repeated. The cuticle of the left front nail 1 was severed and bleeding arrested spontaneously after 3 minutes. 13 Minutes after the start of the first cuticle bleeding time, a bolus infusion of PCPS/Xa was given at a dosage of 40 units/0.05 units/kg body weight. 2 Minutes after the infusion, left front nail 3 was severed and bleeding continued for 12 minutes until arrested by silver nitrate cautery. 60 Minutes after the infusion of PCPS/Xa, left front nail 2 was severed and bleeding arrested spontaneously after 3 minutes. The results obtained are virtually identical to those given in Example 1 and the same conclusion is drawn.

EXAMPLE 3

The same cuticle bleeding time procedure as in Examples 1 and 2 was used in a hemophilic dog (Factor VIII:C level <4%). The right front nail 4 was severed and bleeding continued for 14 minutes until PCPS/Xa at a dosage of 8.0 units and 0.2 units/kg body weight respectively was infused as a bolus. Bleeding stopped abruptly but 2 small rebleeds (1 drop in each case) occurred at 18 and 23 minutes post the start of cuticle bleeding time number 1. 1 Minute prior to the infusion of PCPS/Xa, the right front nail 3 was severed but bleeding arrested 30 seconds after the administration of PCPS/Xa. It should be noted that the observation period was not continued beyond 30 minutes post the start of the cuticle bleeding time number 1. These results demonstrate that the combination of PCPS/Xa, at the dosage used, bypasses Factor VIII in causing the arrest of bleeding in a Factor VIII:C deficient animal. The injured cuticles of such animals would normally bleed until cauterized with silver nitrate. Immediately following the infusion, the animal exhibited apnea and cardiac rhythm irregularities but these resolved spontaneously within 5 minutes after the infusion.

EXAMPLE 4

The procedure of Example 3 was repeated using a different hemophilic animal (Factor VIII:C <1%). The right hind nail 1 was severed and bleeding continued until a bolus infusion of PCPS/Xa at a dosage of 8.0 units and 0.2 units/kg body weight respectively was administered at 16 minutes post the start of the cuticle bleeding time number 1. 1 Minute prior to the administration of PCPS/Xa, the right hind nail 2 was severed but bleeding arrested within 30 seconds of administration of PCPS/Xa. Rebleeding occurred 12 minutes later and continued for 17 minutes until arrested by silver nitrate cautery. 18 Minutes after the administration of PCPS/Xa, the right hind nail 3 was severed and bleeding continued for 12 minutes until arrested by silver nitrate cautery. Immediately following the infusion of PCPS/Xa the animal had a transient cardiopulmonary arrest but regained his vital signs within 2 minutes without resuscitation other than the application of 100% oxygen via a face mask. These results confirm the Factor VIII bypassing activity of a combination of PCPS/Xa at this dosage. The cardiopulmonary side-effects suggest borderline toxicity at this dosage. The rebleeding of right hind nail 2 and the abnormal cuticle bleeding time of right hind nail 3 suggests that the Factor VIII:C bypassing effect is transitory.

EXAMPLE 5

A hemophilic dog, as in Examples 3 and 4 was tested as described above. The right hind nail 2 was severed and bleeding from the cuticle stopped with silver nitrate after 12 minutes. The left hind nail 1 was severed and 2 minutes thereafter PCPS/Xa at a dosage of 4.0 units and 0.1 units/kg body weight respectively was infused. Bleeding continued for a further 10 minutes until arrested by silver nitrate cautery. The animal did not exhibit toxicity but bleeding was not arrested by this dosage of PCPS/Xa.

EXAMPLE 6

The procedure followed in Example 5 was repeated in a different hemophilic dog and with the dose of Factor Xa increased to 0.2 units/kg body weight in combination with PCPS at a dose of 4.0 units/body weight. The right hind nail 1 was severed and bleeding continued for 15 minutes until the PCPS/Xa combination was administered as a bolus infusion. Bleeding stopped abruptly but reoccurred at 27 minutes and continued thereafter until 40 minutes when it was arrested by silver nitrate cautery. 1 Minute prior to the infusion of PCPS, the right hind nail 2 was severed but bleeding ceased within 20 seconds of the infusion of PCPS/Xa combination. Bleeding recommenced 12 minutes later and continued for 13 minutes until arrested with silver nitrate cautery. No cardiopulmonary toxicity was observed. As compared with the result of Examples 3 and 4, a 50% reduction of the dosage of PCPS did not compromise the Factor VIII:C bypassing activity observed in the hemophilic animals. In comparison with Example 5, doubling the dose of Factor Xa in combination with 4 units of PCPS achieved the Factor VIII:C bypass not achieved by the lower dosage of Factor Xa in combination with the same dosage of PCPS.

EXAMPLE 7

The procedure of Example 6 was repeated on another hemophilic dog with the dosage of Factor Xa being maintained but the dosage of PCPS being further reduced to 0.1 unit/kg body weight. The left front nail 5 was severed and bleeding continued for 16 minutes but was arrested abruptly by the infusion of PCPS/Xa. No bleeding occurred during the period of observation. 1 Minute prior to the infusion of PCPS/Xa, the left front nail 4 was severed and bleeding was arrested within 1 minute of the infusion of PCPS/Xa but reoccurred 4 minutes later and continued for 22 minutes until arrested by silver nitrate cautery. 15 Minutes after the infusion of PCPS/Xa, the left front nail 3 was severed and bleeding continued for 12 minutes until arrested by silver nitrate cautery. These results show that a further significant reduction in PCPS/Xa dosage is still associated with Factor VIII bypassing activity but that the effect is less well maintained.

On the basis of these studies, all of which have been carried out on a dog model using Factor Xa derived from bovine blood, it is believed that the minimum dose of Factor Xa required is 0.2 units/kg body weight in conjunction with not less than 1 unit/kg body weight of PCPS vesicles. Tests have confirmed similar results using Factor Xa derived from canine blood and human blood. Infusion of either of these components alone have been shown to have no effect in correcting the cuticle bleeding time of Factor VIII:C deficient animals nor are they thrombogenic. However, it is stressed that Factor Xa in combination with PCPS is an extremely potent reagent and as little as 0.5 units/kg body weight may be sufficiently toxic, i.e. thrombogenic, to cause death. As the combination of Factor Xa and PCPS is synergistic, lower doses of Factor Xa may become toxic (i.e. thrombogenic) when combined with higher doses of PCPS. The examples given suggest that threshold toxicity of Factor Xa at a dosage of 0.02 units/kg body weight is achieved when combined with PCPS at a dosage of 8 units/kg body weight. This ratio of PCPS to Xa (40:1) is considered to be the practical maximum whereas the ratio of PCPS 1 unit to Xa 0.2 units (5:1) is considered to be the practical minimum.

It is also emphasized that these studies have been carried out on a dog model and although this model is believed to simulate the human disease of classical Hemophilia A (Factor VIII:C deficiency) very closely, the specific ratios between, and the actual dosage of, PCPS and factor Xa in the synergistic mixture thereof may vary somewhat from those determined in the dog model.

We claim:

1. A method for controlling hemophilia in mammals comprising administering intravenously to a hemophilic said mammal a synergistic mixture of phospholipid vesicles and mammalian blood factor Xa in relative proportion and in an amount just sufficient to arrest bleeding.

2. A method as claimed in claim 1 wherein said hemophilic mammal is a dog.

3. A method as claimed in claim 2 wherein said phospholipid vesicles are phosphatidylcholine and phosphatidylserine (PCPS).

4. A method as claimed in claim 3 wherein said PCPS is present in said mixture in an amount between about 1 and 8 units per kg of body weight.

5. A method as claimed in claim 4 wherein Factor Xa is present in said mixture in an amount between about 0.2 and less than 0.5 unit per kg of body weight.

6. A method as claimed in claim 3 wherein the ratio of PCPS to Factor Xa is in the range 40:1 to 5:1.

* * * * *